US006670356B2

(12) United States Patent
Davis

(10) Patent No.: US 6,670,356 B2
(45) Date of Patent: Dec. 30, 2003

(54) ANALOGS OF GALANTHAMINE AND LYCORAMINE AS MODULATORS OF NICOTINIC RECEPTORS

(76) Inventor: Bonnie Davis, 160 Cold Spring Rd., Syosset, NY (US) 11791

(*) Notice: Subject to any disclaimer, the term of this patent is extended or adjusted under 35 U.S.C. 154(b) by 0 days.

(21) Appl. No.: 10/148,253

(22) PCT Filed: Dec. 7, 2000

(86) PCT No.: PCT/US00/42654

§ 371 (c)(1),
(2), (4) Date: Aug. 22, 2002

(87) PCT Pub. No.: WO01/43697

PCT Pub. Date: Jun. 21, 2001

(65) Prior Publication Data

US 2003/0050281 A1 Mar. 13, 2003

Related U.S. Application Data

(60) Provisional application No. 60/170,036, filed on Dec. 10, 1999.

(51) Int. Cl.[7] .............................................. A61K 31/55
(52) U.S. Cl. ...................................................... 514/215
(58) Field of Search ......................................... 514/215

(56) References Cited

U.S. PATENT DOCUMENTS

| | | | |
|---|---|---|---|
| 5,312,817 A | 5/1994 | Snorrason | |
| 5,700,480 A | 12/1997 | Hille et al. | 424/448 |
| 5,777,108 A | 7/1998 | Kosley, Jr. et al. | 540/546 |
| 6,150,354 A | 11/2000 | Davis et al. | 514/215 |

OTHER PUBLICATIONS

Nelsen, J. M. and L. Goldstein. "Improvement of performance on an attention task with chronic niocotine treatment in rats." *Psychopharmacologia*, 26: 347–360 (1972).
Wesnes, K., et al., "Effects of nicotine on stimulus sensitivity and response bias in a visual vigilance task." *Neuropsychobiology*, 9: 41–44 (1983).
Peeke, S. C. and H. V. S. Peeke. "Attention, memory and cigarette smoking." *Psychopharmacology*, 84: 205–216, (1984).
Wesnes, K. and D. M. Warburton, "Effects of scopolamine and nicotine on human rapid information processing performance." *Psycopharmacology*, 82: 147–150 (1984).
Warburton, D. M. and K. Wesnes. "Drugs as research tools in psychology: cholinergic drugs and information processing," *Neuropsychobiology*, 11: 121–132 (1984).
Parrott, A. C. and G. Winder. "Nicotine chewing gum (2 mg, 4 mg) and cigarette smoking: comparative effects upon vigilance and heart rate." *Psychopharmacology*, 97: 257–261 (1989).

Sahakain, B., et al., "The effects of nicotine on attention, information processing, and short–term memory in patients with dementia of the Alzheimer type." *British Journal of Psychiatry*, 154: 797–800 (1989).
Rusted, J. and P. Eaton–Williams. "Distinguishing between attentional and amnestic effects in information processing: the separate and combined effects of scopolamine and nicotine on verbal free recall." *Psychopharmacology*, 104: 363–366 (1991).
Parrott, A. C. and D. Craig. "Cigarette smoking and nicotine gum (O, 2 and 4 mg); effects upon four visual attention tasks." *Neuropsychology*, 25: 34–43 (1992).
Warburton, D. M. et al. "A comparison of the attentional and consolidation hypothesis for the facilitation of memory by nicotine." *Psychopharmacology*, 108: 443–447 (1992).
Rusted, J. M. and D. M. Warburton. "Facilitation of memory by post–trial administration of nicotine: evidence for an attentional explanation." *Psychopharmacology*, 108: 454–455 (1992).
Jones, G. M. M., et al. "Effects of acute subcutaneous nicotine on attention, information processing and short–term memory in Alzheimer's disease." *Psychopharmacology*, 108: 485–494 (1992).
Koelega, H. S. "Simulant drugs and vigilance performance: a review." *Psychopharmacology*, 111: 1–16 (1993).
Sahakian, B. J. and J.T. Coull. "Tetrahydroaminoacridine (THA) in Alzheimer's disease: An assessment of attentional and mnemonic function using CANTAB." *Acta Neurol. Scand. 1993: Supplement*, 149: 29–35 (1993).
Bates, T., et al. "Smoking, processing speed and attention in a choice reaction time task." *Psychopharmacology*, 120: 209–212 (1995).
Coger, R. W., et al. "Attention Deficit Disorder in adults and nicotine dependence: psychobiological factors in resistance to recovery." *Journal of Psychoactive Drugs*, 28: 229–240 (1996).
Vidal, C. "Nicotinic receptors in the brain: molecular biology, function, and therapeutics." *Molecular and Chemical Neuropathology*, 28: 3–63 (1996).
Conners, C. K., et al. "Nicotine and attention in Adult Attention Deficit Hyperactivity Disorder (ADHD)." *Psychopharmacology Bulletin*, 32: 67–73 (1996).
Levin, E. D. et al. "Nicotine effects on adults with Attention–Deficit/Hyperactivity Disorder." *Psychopharmacology*, 123: 55–63 (1996).

(List continued on next page.)

*Primary Examiner*—Raymond Henley, III
(74) *Attorney, Agent, or Firm*—Ladas & Parry

(57) ABSTRACT

Analogs of galanthamine and lycoramine are useful in modulating nicotinic receptors in humans and other animals. Modulation of such receptors is useful in treatment and/or prevention of a number of conditions including but not limited to treatment of attention disorders, assistance in giving up smoking and in treatment of Parkinson's disease.

11 Claims, No Drawings

OTHER PUBLICATIONS

Pomerleau, C.S. et al., "Effects of nicotine abstinence and menstrual phase on task performance." *Addictive Behaviors*, 19: 357–362 (1994).

Hughes, J. R. et al. "Effect of tobacco withdrawal on sustained attention." *Addictive Behaviors*, 14: 577–580 (1989).

Edwards, J. A. et al., "Evidence of more rapid stimulus evaluation following cigarette smoking." *Addictive Behaviors*, 10: 113–126 (1985).

Warburton, D. M. "Nicotine as a cognitive enhancer." *Progress in Neuro–Psychopharmacology and Biological Psychiatry*, 16: 181–191 (1992).

Benowitz, N. L. "Pharmacology of nicotine: addiction and therapeutics." *Annual Review Pharmacol. Toxicol.*, 36: 597–613 (1996).

Mangan, G. L. "The effects of cigarette smoking on vigilance performance." *The Journal of General Psychology*, 106: 77–83 (1982).

Periera, E. F. R., et al., "Identification and functional characterization of a new agonist site on nicotinic acetycholine receptors of cultured hippocampal neurons." *The J. of Pharmacology and Experimental Therapeutics*, 165: 1474–1491 (1993).

Storch, A. et al. "Physostigmine, galanthamine and codeine act as 'noncompetitive nicotinic receptor agonists' on clonal rat pheochromocytoma cells." *Eur. J. of Pharmacology, Molecular Pharmacology Section*, 290: 207–219 (1995).

Snorrason, E. et al. "Trial of a selective acetylcholinesterase inhibitor, galanthamine hydrobromide, in the treatment of Chronic Fatigue Syndrome." *J. Chronic Fatigue Syndrome*, 2 (2–3): 35–54 (1996). Presented at the First World Congress of Chronic Fatigue Syndrome and Related Syndrome, Brussels, Nov. 9–11, 1995.

Snorrason, E. and J. G. Stefansson. "Galanthamine hydrobromide in mania." *Lancet*, 337: 557 (1991).

Ranier, M. et al. "Galanthamine hydrobromide in the treatment of senile dementia of Alzheimer's type." *Pharmacological Interventions on Central Cholinergic Mechanisms in Senile Dementia (Alzheimer's Disease)*. Kewitz, Thomsen, Bickel (eds.) W. Zuckshwerdt Verlag Munich, 1989, pp. 233–236.

Vovin, R.Y.a, et al., "Correction of apathabulic manifestations of process defects with cholinotropic compounds", *Zhurnal Nevropatol Psikhiatr*, 2: pp. 111–115 (1991).

Eagger S.A., et al. "Tacrine in Alzheimer's disease", *Lancet*, 337: pp. 989–992 (1991).

Alhainen, K. et al., "Psychometric discrimination of tetrahydroaminoacridine responders in Alzheimer patients", *Dementia*, 4: pp. 54–58 (1993).

Sahakain, B. J., et al. "Further analysis of the cognitive effects of tetrahydroaminoacridine (THA) in Alzheimer's disease: assessment of attentional and mnemonic function using CANTAB", *Psychopharmacology*, 110: pp. 395–401 (1993).

Minthon, L., et al., "Oral tetrahydroaminoacridine treatment of Alzheimer's disease evaluated clinically and by regional cerebral blood flow and EEG", *Dementia*, 4: pp. 32–42 (1993).

ANALOGS OF GALANTHAMINE AND LYCORAMINE AS MODULATORS OF NICOTINIC RECEPTORS

This application claims the benefit of U.S. Provisional Application(s) No(s). 60/170,036 Filing Date: Dec. 10, 1999.

FIELD OF INVENTION

The present invention relates to methods of modulating nicotinic receptors by use of analogs of galanthamine and lycorarmine. Modulation of such receptors is useful in improving attentional functions, relieving pain, treating nicotine and similar addictions, treating anxiety and depression, treating and retarding the progression of Alzheimer's and Parkinson's diseases, neuroprotection against neurodegenerative disorders, alcohol, glutamate and other toxic effects and treatment of schizophrenia.

BACKGROUND OF THE INVENTION

Galanthamine is an alkaloid isolated initially from galanthus nivalis, the snowdrop, which has been used for many years as an acetyleholinesterase inhibitor. The principal use in humans has been the postoperative reversal of neuromuscular blockade. It has also been administered in number of neuromuscular diseases. Because of the activation of muscle, it was of interest to determine the relationship between galanthamine's anticholinesterase activity and its ability to induce twitch potentiation in muscle.

In intact cats, twitch potentiation of the gastrocnemius by direct electric stimulation was measured after intravenous infusion of neostigmine, physostigmine and galanthamine. (Ueda M, Matsumura S, Kimoto S, Matsuda S, Studies on the anticholinesterase and twitch potentiation activities of galanthamine. Jap J Pharmacol 12:111–119, 1962) Galanthamine was 1/10.5× as active as neostigmine and 1/3.5× as active as physostigmine. (p 114) The IC 50 for cholinesterase inhibition, measured in rat brain, erythrocytes, or gastrocnemius homogenate, is in the range of 200 times lower for neostigmine, and 50 times lower for physostigmine than for galanthamine. (Table 4, p 115) This produced a disproportion between the magnitude of twitch potentiation and the enzymatic activity. The authors note "Although the anticholinesterase activity of galanthamine is far inferior to those of neostigmine and physostigmine, the twitch potentiation by galanthamine administration is only ⅟10 of that of neostigmine or physostigmine. So it is presumed that factors other than anticholinesterase activity are concerned with the twitch potentiating effects of galanthamine."

In their discussion, they review this point.

"Although the anticholinesterase activity of galanthamine is about ⅟100 that of neostigmine or physostigmine, the twitch potentiating effects of galanthamine in the nerve muscle preparation is about ⅟10 of the latter. These contradictions between the twitch potentiation and anticholinesterase activity are also not solved by the direct effects of galanthamine on the muscle fibres or by the difference of species in the experimental animals."

The authors consider that the effects of galanthamine may not represent either anticholinesterase activity, or a direct effect, such as would be expected from a depolarizer. They cite the arguments of prior authors that the classical view of acetylcholine accumulation at the neuromuscular junction was inconsistent with "the following points; (1) Potent depolarizers do not necessarily show the marked twitch potentiation. (2) Twitch potentiations caused by anticholinesterase like neostigmine appeared soon after the administration of the compound." Thus, the enhancement of the activity of endogenous transmitter released by electrical stimulation was neither consistent with the time course or potency of anticholinesterases, nor could it be attributed to direct depolarization. Therefore, twitch potentiation was most likely attributable to an action on motor nerve terminals other than enzyme inhibition or direct agonism.

Motor nerve terminals, i.e., the neuromuscular junction, functions by means of a nicotinic cholinergic recepter. Such receptors are found also in ganglia. Kostowski and Gomulka (Note on the ganglionic and central actions of galanthamine, Int J Neuropharmacol, 7:7–14, 1968) investigated the effects of galanthamine and physostigmine on ganglionic transmission in the cat. The drugs were administered intra-arterially and depolarization was recorded from the surface of the superior cervical ganglion. Physostigmine and galantamine were administered in comparable doses, 250 micrograms, which represent fairly equal molarity, as the molecular weight of physostigmine salicylate is 413 and that of galanthamine hydrobromide is 368. As noted above, this represents much greater anticholinesterase potency for physostigmine. As shown in FIG. 1A, p 9, galanthamine, but not physostigmine, substantially inhibited hexamethonium (C6) induced ganglionic blockade. Direct recordings are shown in FIG. 2, p 10, in which preservation of the surface potential is shown in galanthamine, but not physostigmine-treated ganglia. The authors considered that differential penetrability might contribute to these results, but that "the differences in the direct actions of the drugs on ganglionic cholinoceptive sites should also be taken into consideration. In the superior cervical ganglion of the cat, two distinct excitatory cholinoceptive sites have been described . . . The first is activated by nicotine, tetramethylammonium (TMA) and inhibited by curare or hexamethonium-like drugs, whereas the second type is characterized by its sensitivity to muscarine and acetyl-b-methylcholine excitation and to blockade by atropine. Both types of cholinoceptive sites, muscarinic and nicotinic, can be activated by acetylcholine . . . The ability of galantamine to prevent the C6 induced ganglionic blockade suggests that this effect seems to be due to excitation of 'nicotinic cholinoceptive sites'. . . The increase in ganglionic surface potential in ganglia treated with galantamine also supports the hypothesis that such a mechanism is involved in the action of some anticholinesterases."

Recent observations are consistent with the mechanisms proposed by the early authors. Using clonal rat pheochromocytoma (PC12) cells, Storch et al confirmed the conclusions of Ueda more than thirty years earlier. (Storch A, Schrattenholz A, Cooper J C, Abdel Ghani E M, Gutbrod O, Weber K-H, Reinhardt S, Lobron C, Hermsen B, Soskic V, Periera E F R, Albuquerque E X, Methfessel C, Maelicke A, Physostigmine, galanthamine and codeine act as 'noncompetitive nicotinic receptor agonists' on clonal rat pheochromocytoma cells. Eur J Pharmacol Mol Pharmacol Sect 290:207–219, 1995)

The authors note that "physostigmine, galanthamine and codeine do not evoke sizable whole-cell currents, which is due to the combined effects of low open-channel probability, slow onset and slow inactivation of response." These agents require an ion channel which has been opened, as can be done by a direct agonist, in order to have an effect. Physostigmine and galanthamine do, however, cause some channel activation in inside-out patches from PC 12 cells. This activation can also be produced by acetylcholine. Methyllycaconitine, a competitive nicotinic antagonist, blocks the activation by acetylcholine, but not by the cholinesterase inhibitors. (FIG. 2, p 211) Galanthamine and physostigmine are, therefore, not binding at the agonist site. On the other hand, after incubation with FK1, a competitive monoclonal antibody to physostigmine, neither physostigmine nor galanthamine could induce single channel activity, while acetylcholine still could. The authors conclude "In other words, (−)-physostigmine (and galanthamine) [that is the authors's addition in parentheses] acted as noncompetitive agonists at nicotinic receptors of PC12 cells." (p213)

Thus, the ability of galanthamine to enhance activation of motor nerve terminals stimulated electrically, to increase ganglionic depolarization induced by acetylcholine and to protect against hexamethonium, indicating enhancement of the activity of nicotinic receptors, has been confirmed with the newer methods of patch-clamp and antibody techniques.

SUMMARY OF THE INVENTION

The present invention provides a method for modulating nicotinic by administering an effective amount of a galanthamine or lycoramine analog to a patient in need of such modulation.

DETAILED DESCRIPTION OF THE INVENTION

Analogs of galanthamine that are of use in the present invention are those having good nicotinic properties. Classical neurochemical techniques, such as employed by Kostowski and Gomulka (op cit) may be used to identify compounds with nicotinic properties. In these, an outcome measure known to be cholinergic, such as an electrical potential or other biological function, is blocked with a nondepolarizing agent such as hexamethonium. Newer techniques, such as patch-clamp recordings in hippocampal slices (Alkondon M, Pereira E F, Eisenberg H M, Albuquerque E X, Choline and selective agonists identify two subtypes of nicotinic acetylcholine receptors that modulate GABA release from CA1 interneurons in rat hippocampal slices. J Neurosci 19(7):2693–2705, 1999), current and voltage clamp modes, (Frazier C J, Rollins Y D, Breese C R, Leonard S, Freedman R, Dunwiddie T V (Acetylcholine activates an alpha-bungarotoxin-sensitive nicotinic current in rat hippocampal interneurons, but not pyramidal cells. J Neurosci 18(4)1187–1195, 1998) or electrophysiological recordings (Stevens K E, Kem W R, Freedman R, Selective alpha 7 nicotinic receptor stimulation normalizes chronic cocaine-induced loss of hippocampal sensory inhibition of C3H mice. Biol Psychiatry 46(10)1443–50, 1999), or techniques such as employed by Storch et al, above, may be also be used to identify compounds which are candidates for appropriate safety, pharmacokinetic and finally studies in humans. In addition, pharmacological reversal trials with nicotinic receptor inhibitors such as hexamethonium mecamylamine, methylyaconitine dihydro beta erythroidine may be used to identify nicotinic mechanisms.

Such compounds include analogs wherein at least one of the methoxy, hydroxy or methyl groups of galanthamine or lycoramine is replaced as follows:

the methoxy group by another alkoxy group of from one to six carbon atoms, a hydroxy group, hydrogen, an alkanoyloxy group, a benzoyloxy or substituted benzoyloxy group, a carbonate group or a carbamate group or a trialkylsilyloxy group;

the hydroxy group by an alkoxy group of from one to six carbon atoms, hydrogen, an alkanoyloxy group, a benzoyloxy or substituted benzoyloxy group, a carbonate group or a carbamate group;

the N-methyl group by hydrogen, alkyl, benzyl, cyclopropylmethyl group or a substituted or unsubstituted benzoyloxy group.

Other suitable analogs may be found for example in International Patent Publication W088/08708 and an article by Bores and Kosley in Drugs of the Future 21:621–631 (1996).

Alkanoyloxy, carbamate and carbonate groups of use in the compounds of the present invention typically contain up to ten carbon atoms. The substituent groups, are typically selected from alkyl or alkoxy groups of from 1 to 6 carbon atoms, halo groups, and haloalkyl groups such as trifluoromethyl. When reference is made to alkyl groups, where the context permits, the term also include groups which are or contain cycloalkyl groups including adamantyl groups. Aryl groups are typically phenyl or naphthyl but may include heteroaryl such as morpholino. The carbamate groups may be mono or di-substituted and in the case of disubstituted carbamates, each of the groups may be as just specified. For example a dimethyl carbamate group may be used.

Galanthamine has the following structure:

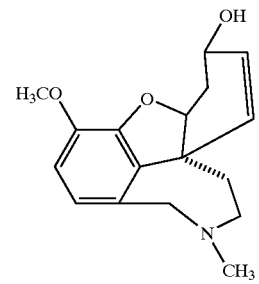

Lycoramine is similar but has only a single bond between the 3 and 4 positions.

Particularly useful analogs of galanthamine and lycoramine for use in the present invention include analogs thereof wherein the hydroxy and/or methoxy groups are replaced by carbamate groups, for example 2-n-butyl carbamates.

Other compounds that may be of use are those wherein the methoxy group of galanthamine or lycoramine is replaced by a hydrogen, hydroxy or alkoxy group of from two to six carbon atoms or an acyloxy group, for example an alkanoyloxy or benzoyl group, of from one to seven carbon atoms, more preferably of two to seven carbon atoms. Other compounds that may be of interest are those wherein the methoxy group is replaced by a mono or dialkyl carbamate or carbonate group wherein the alkyl groups contain from 1 to 8 carbon atoms, preferably of from 4 to 6 carbon atoms or wherein the methoxy group thereof is replaced by an aryl carbamate or carbonate group wherein said aryl group is selected from phenyl, naphthyl, substituted phenyl and substituted naphthyl groups wherein said substituent is selected from alkyl and alkoxy groups of from 1 to 6 carbon atoms, trifluoro methyl groups and halo groups. Care should, however, be taken with such 13-carbamates to ensure that there are no toxicity problems with the intended method of use.

Other useful analogs include compounds wherein, independently of whether or not the methoxy group has been replaced, the hydroxy group is replaced by an alkoxy group of from one to six carbon atoms, hydrogen, an acyloxy group, for example an alkanoyloxy group, typically of from 1 to 7 carbon atoms, a benzoyloxy or substituted benzolyloxy group wherein said substituent is selected from alkyl and alkoxy groups of from 1 to 6 carbon atoms, trifluoro methyl groups and halo groups, or a carbonate group, preferably or a carbamate group which may be a mono or dialkyl or an aryl carbamate or carbonate wherein the alkyl groups contain from 1 to 8 carbon atoms, preferably of from 4 to 6 carbon atoms or said aryl group is selected from phenyl, naphthyl, substituted phenyl and substituted naphthyl groups wherein said substituent is selected from alkyl and alkoxy groups of from 1 to 6 carbon atoms, trifluoro methyl groups and halo groups.

Analogs of galanthamine may be developed to enhance nicotinic receptor modulation relative to cholinesterase inhibiting ability. These could be useful in a large number of conditions, reviewed by Lena and Changeux. (Lena C and Changeux J-P, Pathological mutations of nicotinic receptors and nicotine-based therapies for brain disorders. Current Opinion in Neurobiology 7:674–682, 1997) Congenital myasthenia gravis, some cases of which are due to increase of function in the muscle nicotinic receptor, could benefit from an analog with allosteric inhibitory properties. Other diseases associated with functional point mutations in nicotinic receptors are autosomal dominant frontal lobe epilepsy and human hereditary hyperekplexia.

In Alzheimer's disease, nicotine has been shown to enhance cognition. Moreover, demographic and laboratory evidence suggests neuroprotective properties of nicotine in Alzheimer's disease, in Parkinson's disease, where therapeutic effects have also been reported, and against neurotoxic manipulations such as glutamate administration, nerve growth factor deprivation, and ethanol administration. (See also Court J A, Lloyd S, Perry R H, Griffiths M, Morris C, Johnson J, McKeith I G, Perry E K, The nicotinic cholinergic system and beta-amyloidosis, in Alzheimer Disease: From Molecular Biology to Therapy, Becker R and Giacobini E, eds, Birkhauser, Boston, 1996; Kihara T, Shimohama S, Akaike A, Nicotinic receptor stimulation protects neurons against glutamate- and amyloid-beta-induced cytotoxicity, in Alzheimer's Disease and Related Disorders, Iqbal K, Swaab D F, Winblad B and Wisniewski H M, eds, John Wiley & Sons Ltd, Chichester, 1999; Yamashita H and Nakamura S, Nicotine rescues PC12 cells from death induced by nerve growth factor deprivation. Neuroscience Letters 213:145–147, 1996; Li Y, Meyer E M, King M A, Nicotinic receptor mediated signal transduction against ethanol and amyloid cytotoxicity, Abstract No. 394.17, Society for Neuroscience, Volume 25, 1999). Thus, augmentation of nicotinic receptor function may produce functional improvements in Alzheimer's disease and Parkinson's disease and reduce neurodegeneration.

Compounds that could eliminate or reduce nicotine dependence, or that of other drugs operating through the same brain mechanisms, in smokers would be useful. Nicotinic drugs may also be of value in the treatment of Tourette's Syndrome, and to improve attention. A particular attentional deficit, auditory gating, (although other attentional paradigms show similar results) found commonly in schizophrenia but also in 50% of first-degree relatives, can be reversed by nicotine. Thus, analogs with nicotinic properties may be employed in a variety of situations in which it is desirable to normalize or improve attentional functions.

Dosages for suitable agents can be determined by standard techniques such as those set out for example in Chapter 6 (by Benjamin Calesnick) of Drill's Pharmacology in Medicine (Fourth Edition Joseph R. DiPalma ed, McGraw-Hill 1971 or in Chapter 6 (by B. E. Rodda et al) of Biopharmaceutical Statistics for Drug Development (ed. Karl E. Peace, Marcel Dekker Inc. 1988).

What is claimed is:

1. A method for modulating nicotinic activity by administering an effective amount of a galanthamine analog or a lycoramine analog to a patient in need of such modulation.

2. A method as claimed in claim 1 wherein said analog of galanthamine or lycoramine is one wherein at least one of the methoxy, hydroxy or methyl groups of galanthamine or lycoramine is replaced as follows:

the methoxy group by another alkoxy group of from one to six carbon atoms, a hydroxy group, hydrogen, an alkanoyloxy group, a benzoyloxy or substituted benzoyloxy group, a carbonate group or a carbamate group or a trialkylsilyloxy group;

the hydroxy group by an alkoxy group of from one to six carbon atoms, hydrogen, an alkanoyloxy group, a benzoyloxy or substituted benzoyloxy group, a carbonate group or a carbamate group;

the N-methyl group by hydrogen, alkyl, benzyl, cyclopropylmethyl group or a substituted or unsubstituted benzoyloxy group.

3. A method as claimed in claim 2 wherein any alkanoyloxy, carbamate and carbonate group present contains up to ten carbon atoms.

4. A method as claimed in claim 2 wherein any of said alkanoyloxy, carbamate or carbonate group comprises an alkyl or alkoxy group of from 1 to 6 carbon atoms optionally substituted by one or more halo groups.

5. A method as claimed in claim 2 wherein said analog is a galanthamine analog.

6. A method as claimed in claim 2 wherein said analog is a lycoramine analog.

7. A method as claimed in claim 2 wherein said analog is an n-butyl carbamate.

8. A method as claimed in claim 2 wherein the methoxy group of galanthamine or lycoramine is replaced by a hydrogen, hydroxy or alkoxy group of from two to six carbon atoms or an acyloxy group or a mono or dialkyl carbamate or carbonate group wherein the alkyl groups contain from 1 to 8 carbon atoms.

9. A method as claimed in claim 2 wherein the hydroxy group of galanthamine or lycoramine is replaced by an alkoxy group of from one to six carbon atoms, hydrogen, an acyloxy group, a carbonate group or a carbamate group which may be a mono or dialkyl or an aryl carbamate or carbonate wherein the alkyl groups contain from 1 to 8 carbon atoms.

10. A method as claimed in claim 2 wherein the compound employed is one wherein the hydroxyl group of galanthamine or lycoramine is replaced by a n alkanoyl group of 2 to 7 carbon atoms, a mono or dialkyl carbamate of one to 1–8 carbon atoms per alkyl group, a mono or diaryl carbamate, an alkyl carbonate of one to six carbon atoms in its alkyl group or an aryl carbonate.

11. A method as claimed in claim 2 or 10 wherein the compound employed is one wherein the methoxy group of galanthamine or lycoramine is replaced by an alkoxy group of two to six carbon atoms or a carbonate of from one to six carbon atoms an alkyl carbonate of one to six carbon atoms in its alkyl group or an aryl carbonate.

* * * * *